United States Patent
Wherritt

(10) Patent No.: US 9,739,740 B2
(45) Date of Patent: Aug. 22, 2017

(54) PERMITTIVITY SENSOR

(75) Inventor: Peter Wherritt, Abingdon (GB)

(73) Assignee: Salunda Limited (GB)

(*) Notice: Subject to any disclaimer, the term of this patent is extended or adjusted under 35 U.S.C. 154(b) by 142 days.

(21) Appl. No.: 13/809,828

(22) PCT Filed: Jul. 13, 2011

(86) PCT No.: PCT/GB2011/001055
§ 371 (c)(1),
(2), (4) Date: Mar. 18, 2013

(87) PCT Pub. No.: WO2012/007718
PCT Pub. Date: Jan. 19, 2012

(65) Prior Publication Data
US 2013/0176038 A1    Jul. 11, 2013

(30) Foreign Application Priority Data

Jul. 13, 2010 (GB) .................................... 1011785.1

(51) Int. Cl.
G01R 27/26    (2006.01)
G01N 27/22    (2006.01)
G01N 33/28    (2006.01)

(52) U.S. Cl.
CPC ....... G01N 27/221 (2013.01); G01N 33/2829 (2013.01)

(58) Field of Classification Search
CPC .... G01R 27/26; G01R 27/08; G01R 27/2617; G01R 27/2623; G01N 27/26;
(Continued)

(56) References Cited

U.S. PATENT DOCUMENTS 2,906,950 A * 9/1959 Ichijo .................... G01R 27/02
324/243
3,120,647 A * 2/1964 Bravenec ................. H03B 5/20
324/76.52
(Continued)

FOREIGN PATENT DOCUMENTS

EP    0 411 204 A1    2/1991
EP    2 009 434 A2    12/2008
(Continued)

OTHER PUBLICATIONS

L.E. González Prieto, et al., "Electric properties of biodiesel in the range from 20 Hz to 20 MHz. Comparison with diesel fossil fuel", *International Journal of Hydrogen Energy*, vol. 33, No. 13, Jul. 1, 2008, pp. 3531-3537.

(Continued)

*Primary Examiner* — Arleen M Vazquez
*Assistant Examiner* — Steven Yeninas
(74) *Attorney, Agent, or Firm* — Brinks Gilson & Lione

(57) ABSTRACT

Fluid sensor and method comprising: an oscillator having operating characteristics. Permittivity sensing element coupled to the oscillator and arranged to alter the operating characteristics of the oscillator in response to changes in permittivity presented to the permittivity sensing element. Reference element comprising an electrical impedance having a real and imaginary component controllably coupled to both the oscillator and the permittivity sensing element and arranged to alter the operating characteristics of the oscillator.

Method of measuring the composition of a fuel comprising the steps of: measuring a real permittivity of the fuel. Measuring an imaginary permittivity of the fuel. Determining a proportion of biodiesel in the fuel based on the
(Continued)

measured real permittivity. Determining a proportion of unrefined oil in the fuel based on the measured imaginary permittivity.

17 Claims, 4 Drawing Sheets

(58) Field of Classification Search
CPC .. G01N 27/221; G01N 33/28; G01N 33/2829; G01N 27/02; G01N 27/028; G01N 27/06; G01N 27/22; G01N 27/2605; G01K 7/34; G01K 7/343
USPC ....... 324/675, 652, 663, 682, 683, 674, 685, 324/693, 333, 668, 332, 439, 33, 61, 658, 324/659, 664, 667, 694, 696, 698, 442; 73/61.43, 61.44, 61.42, 61.41, 61.61; 340/540, 620, 562, 603, 606, 612, 618; 331/65

See application file for complete search history.

(56) References Cited

U.S. PATENT DOCUMENTS

| | | | |
|---|---|---|---|
| 3,671,857 A | 6/1972 | Bergmanis et al. | |
| 3,896,374 A * | 7/1975 | Delafon | G01R 27/2605 324/679 |
| 4,112,744 A | 9/1978 | Tassano | |
| 4,399,404 A | 8/1983 | Resh | |
| 4,426,616 A * | 1/1984 | Maier | G01R 27/26 324/658 |
| 4,450,437 A * | 5/1984 | Ho | G08B 21/0415 340/540 |
| 4,528,655 A * | 7/1985 | Tamura | G11B 9/06 324/661 |
| 4,560,923 A * | 12/1985 | Hanson | G01N 27/223 324/601 |
| 4,609,870 A * | 9/1986 | Lale | G01N 27/9053 324/225 |
| 4,652,819 A * | 3/1987 | Kammerer | H03K 17/9502 307/116 |
| 4,844,623 A * | 7/1989 | Wada | G01K 7/245 374/171 |
| 4,847,551 A * | 7/1989 | Bose | G01R 27/2605 324/679 |
| 5,198,777 A * | 3/1993 | Masuda et al. | 324/671 |
| 5,245,295 A * | 9/1993 | Hata et al. | 324/683 |
| 5,245,873 A * | 9/1993 | Fathauer | G01F 23/266 307/118 |
| 5,418,466 A | 5/1995 | Watson et al. | |
| 5,483,172 A * | 1/1996 | Radford | 324/693 |
| 5,594,163 A * | 1/1997 | Suzuki | G01N 27/221 73/61.44 |
| 6,545,603 B1 | 4/2003 | Launay et al. | |
| 8,159,234 B2 * | 4/2012 | Niwa | H03K 17/9502 324/207.16 |
| 2006/0158200 A1 * | 7/2006 | Eilersen | G01R 27/2605 324/667 |
| 2009/0001997 A1 * | 1/2009 | Lin et al. | 324/675 |
| 2009/0115434 A1 | 5/2009 | Hirthe et al. | |
| 2010/0225332 A1 * | 9/2010 | Niwa | H03K 17/9547 324/652 |
| 2010/0231239 A1 * | 9/2010 | Tateishi | G01D 5/24 324/672 |
| 2011/0128014 A1 * | 6/2011 | Harrison | G01D 5/145 324/601 |
| 2011/0267078 A1 * | 11/2011 | Eilersen | G01R 27/2605 324/658 |

FOREIGN PATENT DOCUMENTS

| | | |
|---|---|---|
| WO | WO 02/093150 A1 | 11/2002 |
| WO | WO 2004/113897 A1 | 12/2004 |
| WO | WO 2005/109012 A1 | 11/2005 |

OTHER PUBLICATIONS

Flavia C.C. Oliveira, et al., "Adulteration of diesel/biodiesel blends by vegetable oil as determined by Fourier transform (FT) near infrared spectrometry and FT-Raman spectroscopy", *Analytica Chimica Acta*, vol. 587, No. 2, Mar. 28, 2007, pp. 194-199.

Christopher J. Chuck, et al., "Spectroscopic sensor techniques applicable to real-time biodiesel determination", *Fuel*, vol. 89, No. 2, Feb. 1, 2010, pp. 457-461.

International Search Report and Written Opinion for PCT/GB2011/001055 mailed Jan. 27, 2012.

\* cited by examiner

PERMITTIVITY SENSOR

CROSS-REFERENCE TO RELATED APPLICATION

This application is a filing under 35 U.S.C. §371 of International Patent Application PCT/GB2011/001055, filed Jul. 13, 2011, which claims priority to Great Britain Application No. 1011785.1, filed Jul. 13, 2010. The contents of International Patent Application PCT/GB2011/001055 are incorporated by reference in their entirety.

FIELD OF THE INVENTION

The present invention relates to a permittivity sensor and in particular a sensor used to measure the constituents of a fluid and for improving the stability of such a sensor.

BACKGROUND OF THE INVENTION

Measurement of the properties of a liquid or other samples may be done by sampling and laboratory analysis, using chemical or optical instrumentation, depending on what is to be measured. For example, FTIR or gas chromatography may be used. Examples of liquids measured in this way include water in hydrocarbons (fuels and oils), fuel mixtures, chemical concentration and water contamination. While laboratory analysis of samples produces accurate measurement the process is time consuming and relatively expensive. Furthermore, such laboratory analysis cannot be made in real-time or in-situ.

The use of fuel mixtures such as diesel and biodiesel results in particular problems when the composition of these mixtures is measured. Certain engines require that their fuel mixture ratio is within certain tolerances and damage or premature failure may occur if these tolerances are exceeded.

For example, the biodiesel content of diesel fuel and contamination with unrefined vegetable oil may require constant checking and verification. Unrefined vegetable oil is often used as a cheap fuel substitute for diesel trucks and cars as it is the raw material biodiesel is derived from and will combust readily in a diesel engine. However, fuel adulterated with high levels of unrefined oil may seriously damage modern diesel engines and often leads to engine failure within the warranty period of the vehicle. Also there is a requirement for quality sensors to determine the concentration of Urea in aqueous solution for use in NOx catalytic reduction systems. Also there is a requirement for quality sensors to measure oxidation of lubricating oil. Therefore, a real-time sensing mechanism is required.

A permittivity sensor driven by an oscillator may be used to measure electrical properties of a liquid in real time. These measurements may be used to infer the composition of the liquid. However, where the composition of a mixture includes different liquids having a similar electric permittivity then such a sensor may not be able to distinguish between the constituents of the liquid.

Furthermore, drift—both short term and long term—may be an inherent property of oscillators and is such that it is difficult to make absolute measurements without some form of reference system. Switching to some reference, be it a reference fluid (pure known liquid) or a dummy reference, may be used. However, it can take some time for the oscillator to stabilise when switched form one load to the reference. In the meantime, the composition of the liquid may have changed by an undesirable amount.

Electronic sensors have been developed to monitor fluids. Most of these devices are one-parameter devices that usually measure a parameter that is proportional to the dielectric constant of the sample. These are generally known as capacitive sensors. A disadvantage of these single parameter systems is that the scope of what can be detected is often rather limited and depends on the sample being very controlled, which is often unrealistic in practice.

EP2009434 describes a system for determining the concentration of biodiesel in a mixture of biodiesel and petrodiesel by measuring the amplitude and frequency of a resonant circuit. However, EP2009434 does not describe how to detect unrefined oil in the biodiesel or how to improve calibration.

Therefore, there is required a sensor that overcomes these problems and meets these requirements.

SUMMARY OF THE INVENTION

In accordance with a first aspect of the present invention there is provided a permittivity sensor comprising:
an oscillator having operating characteristics;
a permittivity sensing element coupled to the oscillator and arranged to alter the operating characteristics of the oscillator in response to changes in permittivity presented to the permittivity sensing element; and
a reference element switchably coupled to both the oscillator and the permittivity sensing element and arranged to alter the operating characteristics of the oscillator. The reference element is coupled to the oscillator and the permittivity sensing element at the same time when a switch is closed. When the switch is opened, the reference element is simultaneously disconnected from the oscillator and from the permittivity sensing element.

Optionally, the permittivity sensing element may be a capacitive sensing element or an inductive sensing element.

Optionally, the reference element may comprise a capacitor and a resistor or an inductor. In other words, the reference element may be capacitive (capacitor and resistor pair) or inductive (inductor).

Preferably, the oscillator may be a positive Robinson marginal feedback oscillator but other oscillators may be used.

Preferably, the reference element may be switchably coupled in parallel to the permittivity sensing element and the oscillator.

Optionally, the permittivity sensor may further comprise a reference resistor switchably coupled to the oscillator and the permittivity sensing element, and/or the reference element. This reference resistor is a further reference or calibration device to be introduced into the circuit. The switching configuration includes coupling the permittivity sensing element, the oscillator and the reference resistor together; coupling the permittivity sensing element, the oscillator, the reference element and the reference resistor together; and coupling the oscillator and the permittivity sensing element together.

Preferably, the oscillator may be arranged to provide a resonance frequency to the permittivity sensing element. The change in resonance frequency may be measured to determine properties of a sample.

Optionally, the permittivity sensor may further comprise a processor arranged to compare the operating characteristics of the oscillator when the reference element is coupled to the oscillator and permittivity sensor element to the operating characteristics of the oscillator when the reference element is not coupled to the oscillator and permittivity sensor element. This allows for drift or calibration errors to be determined and accounted for.

Optionally, the processor may be further arranged to calibrate the permittivity sensor element based on the comparison of oscillator operating characteristics.

Optionally, the operating characteristics include any one or more selected from the group consisting of frequency, amplitude, Q-value and phase.

Preferably, the permittivity sensor may further comprise a first output that varies with a first operating characteristic of the oscillator as a real component of the permittivity presented to the permittivity sensing element changes. The real component of permittivity may vary with one or more properties of a sample being measured, for example, the concentration of one constituent of the sample.

Preferably, the permittivity sensor further comprises a second output that varies with a second operating characteristic of the oscillator as an imaginary component of the permittivity presented to the permittivity sensing element changes. The imaginary component of permittivity may vary with one or more properties of a sample being measured, for example, the concentration of one constituent of the sample relative to another or the presence of impurities.

Preferably, the first operating characteristic may be frequency.

Preferably, the second operating characteristic may be voltage.

In accordance with a second aspect of the present invention there is provided a method of measuring the permittivity of a sample comprising the steps of:

driving a permittivity sensing element with an oscillator having driving characteristics;

presenting a sample to the permittivity sensing element;

measuring the driving characteristics;

altering the driving characteristics by switchably coupling a reference element to both the permittivity sensing element and the oscillator; and measuring the altered driving characteristics. This improves measurement repeatability especially where environmental conditions (e.g. temperature and pressure) change between measurements. The driving characteristics of the oscillator may be operating characteristics such as frequency, resonance frequency, voltage or quality factor (Q), for example. Furthermore, as the permittivity sensing element remains coupled and driven by the oscillator whilst the reference element is switched in then there is less overall disturbance on the circuit and less time to recover when the reference element is removed or switched out.

Preferably, the method may further comprise the step of:

providing a first output that varies with a first operating characteristic of the oscillator as a real component of a permittivity of the sample presented to the permittivity sensing element changes.

Preferably, the method may further comprise the step of:

providing a second output that varies with a second operating characteristic of the oscillator as an imaginary component of a permittivity of the sample presented to the permittivity sensing element changes. Various components of a sample may have different real and imaginary permittivity and this can be used to determine the concentration or presence of each component.

Preferably, the first operating characteristic may be frequency.

Preferably, the second operating characteristic may be voltage.

Optionally, the method may further comprise the steps of:

altering the driving characteristics by switchably coupling a reference resistor to both the permittivity sensing element and the oscillator;

preferably decoupling the reference element from the permittivity sensing element; and measuring the altered driving characteristics. The as the permittivity sensing element remains coupled to the oscillator whilst the reference resistor is switched in, there is less disturbance of the driving oscillations.

In accordance with a third aspect of the present invention there is provided a fuel composition sensor comprising:

an oscillator;

a permittivity sensor coupled to the oscillator and arranged to measure the real and imaginary components of permittivity of fuel proximate with the permittivity sensor; and a processor arranged to monitor the measured real and imaginary components of the permittivity and in response provide an output indicative of the fuel composition. Certain fuel components may affect the real permittivity, whilst other fuel components may affect the imaginary permittivity. Therefore, measuring both can provide additional information about the fuel being tested. Sample measurements on known compositions or likely individual components or impurities may be made in advance and used as calibration data, for example. This fuel composition sensor may be incorporated into an engine, vehicle or separate fuel supply system.

In accordance with a fourth aspect of the present invention there is provided a method of measuring the composition of a fuel comprising the steps of:

measuring a real permittivity of the fuel;

measuring an imaginary permittivity of the fuel;

determining a proportion of biodiesel in the fuel based on the measured real permittivity; and determining a proportion of unrefined oil in the fuel based on the measured imaginary permittivity.

Optionally, measuring the real permittivity and the imaginary permittivity may further comprise the steps of providing a permittivity sensing element driven by an oscillator having operating characteristics.

Preferably, the operating characteristics may include any of amplitude, frequency, voltage and Q-factor.

Optionally, any processing of measured data may be carried out on a computer, dedicated electronic logic, internal or external processor, or analogue or digital means.

It should be noted that any feature described above with respect to one aspect may be used with any other particular aspect or embodiment of the invention.

BRIEF DESCRIPTION OF THE FIGURES

The present invention may be put into practice in a number of ways and embodiments will now be described by way of example only and with reference to the accompanying drawings, in which.

Figure 1:
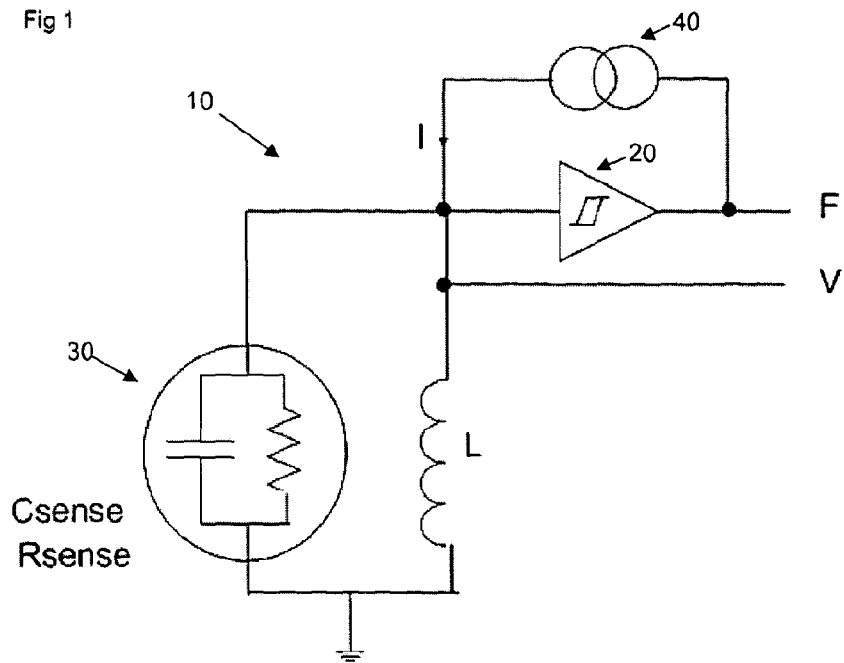
FIG. 1 shows a schematic diagram of a circuit used to measure the real and imaginary permittivity of a sample, given by way of example only.

It should be noted that the figures are illustrated for simplicity and are not necessarily drawn to scale.

DETAILED DESCRIPTION OF THE PREFERRED EMBODIMENTS

Where the likely constituents of a liquid are known (e.g. water and hydrocarbon) and the range of proportions of the two components of the liquid mixture has already been characterised, then it is possible to use real and imaginary permittivity as a measure of the ratio. This technique is more difficult to implement where there are a number of variables or unknown variables. However, it can still be used to detect change in a process without necessarily being able to identify what the change is caused by.

The real and imaginary permittivity of a liquid may be measured at either a single frequency, or at a number of selected frequencies or by frequency sweeping, for example. Appropriate frequencies depend on the characteristics of the liquid and what is required to be measured, but typically fall in the MHz to GHz band.

A radiofrequency (RF) sensor able to measure simultaneously both real and imaginary permittivity in real time can be made with a resonant LC tank circuit and an oscillator, for example, preferably of a positive feedback type.

One component of the LC tank circuit, typically the capacitive element, may be in contact or close proximity with the liquid to be measured. Changes in the real permittivity change the capacitance and hence the resonance frequency. Changes in the imaginary permittivity affect the amplitude or voltage of the oscillator.

Measurements may be of two kinds, absolute measurement of a liquid mixture, for example the ratio of biodiesel in diesel or change as in a process. The accuracy of either of these measurements may be dependent upon the stability of the oscillator frequency. According to one implementation, there is a requirement to be able to detect extremely small (sub 100 ppm) amounts of water, methanol and biofuels in jet fuel and other hydrocarbons.

A positive feedback oscillator, for example, may be used to excite a resonant circuit of which one component is a permittivity sensing element, which responds to the presence of the material being sensed. The sensing element presents a complex impedance to the resonant circuit, whereby its resistive and reactive properties change with the material being sensed.

Positive feedback oscillators may be used and over the approximate frequency range of 1 to 100 MHz (or greater), for example. The permittivity sensing element or sensor may be part of a tuned circuit that is the load of the oscillator. Two parameters may be derived from the sensor system as a whole: the resonance frequency of the oscillator and a voltage that is proportional to the voltage across the oscillator tank circuit.

For fluids, and applications in this frequency range, the sensing element used may form the capacitive part of the tank circuit. The sample properties measured may be generally changes in the complex electrical permittivity of the fluid. The real part of the electrical permittivity is equivalent to the dielectric constant of the material being tested. The imaginary part is a measure of radiofrequency losses within it.

When considering the example of biodiesel, the real electrical permittivity of biodiesel and unrefined vegetable oil are very similar, so a single parameter device could be designed to measure the overall level of both biodiesel and unrefined oil within a sample but such a system would be unable to distinguish between the two. Therefore, this limits the potential use of the device. However, the imaginary permittivity of biodiesel and unrefined oil are significantly different. These differences may be used to detect the biodiesel percentage and also identifies the presence of significant amounts of unrefined oil. In other words, measuring these two parameters enables measurements to be made on more complex samples without the use of laboratory equipment.

The use of positive feedback further simplifies the system. One reason for this is that the two measured parameters (frequency and tank voltage) can be set up so that these are predominantly dependent on the real and imaginary parts of the electrical permittivity respectively, i.e. there is no significant crosstalk between the two parameters. This further simplifies data analysis and interpretation.

One disadvantage of oscillator based sensors is a tendency for the resonance frequency (and the tank voltage) to drift with time and temperature. Although the positive feedback oscillators may reduce such drift, it is difficult for it to be eliminated.

Therefore, the system may further include features to compensate or calibrate for such drift.

As shown in FIG. 1, a positive feedback oscillator 10 requires a resonant circuit comprising at least two components (usually a capacitor and an inductor L) together with driving electronics (usually a limiting amplifier 20) to energise the resonant circuit with a current I. The oscillator 10 is driven by a current source 40. These components all contribute to the actual frequency F and voltage V produced by the circuit 10. The example shows a capacitive sensing element 30 but the principles apply equally to an inductive sensing element.

In a sensing application changes in the complex impedance of the sensing element 30 are of interest. The reactive component (in this case capacitance Csense) determines the frequency F and the real component (the resistance Rsense) determines the voltage V. Changes in these parameters reflect changes in the material being sensed.

However, changes in the resonant inductor L and the driving electronics with time or temperature may adversely affect the accuracy of the system as they also alter the oscillator voltage frequency F.

Figure 2:
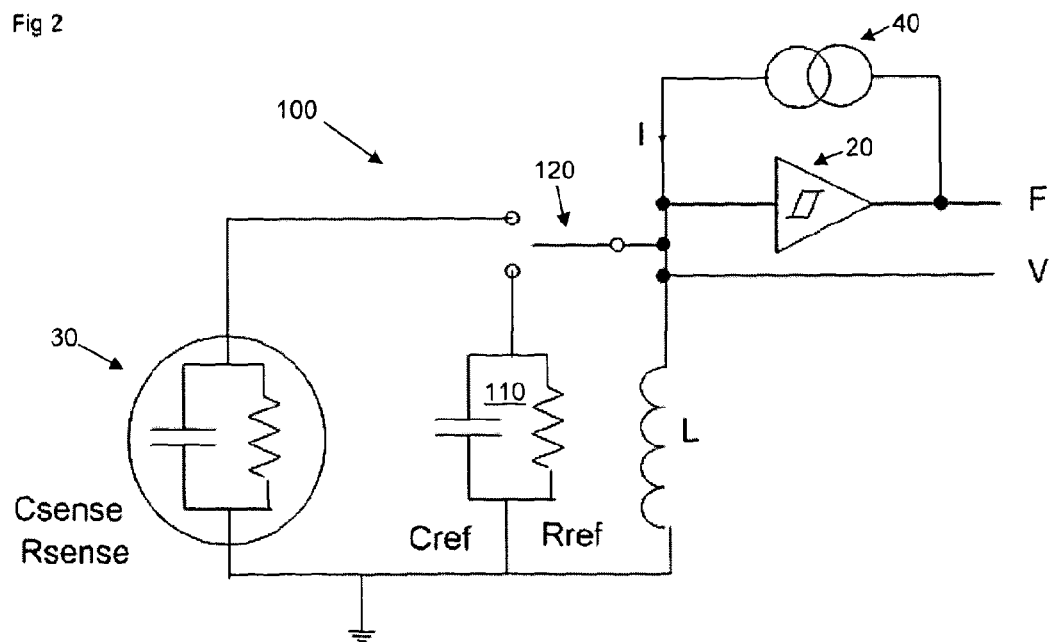
FIG. 2 shows a schematic diagram of a further circuit used to measure the real and imaginary permittivity of a sample and incorporating a reference circuit.

As shown in FIG. 2, one approach is to use a reference resonant circuit 110 made using high stability components, Cref, Rref, and switch the same electronics between this reference circuit 110 and the sensing circuit 30 using switch 120 (similar features in different figures are provided with the same reference numerals).

Since the same inductor L and electronics are used by both the sensing circuit 30 (formed from Csense and Rsense) and the reference circuit 110 (formed from Cref and Rref), the actual impedance (real and reactive components) of the sensing circuit 30 can be expressed in terms of the reference circuit impedance (real and imaginary components). This renders the circuit 100 largely independent of changes in the resonant inductor L or drive electronics.

However, this simple approach has problems because the oscillator operation may be disrupted during the switchover and stable measurements may not be quickly or easily obtained.

Figure 3:
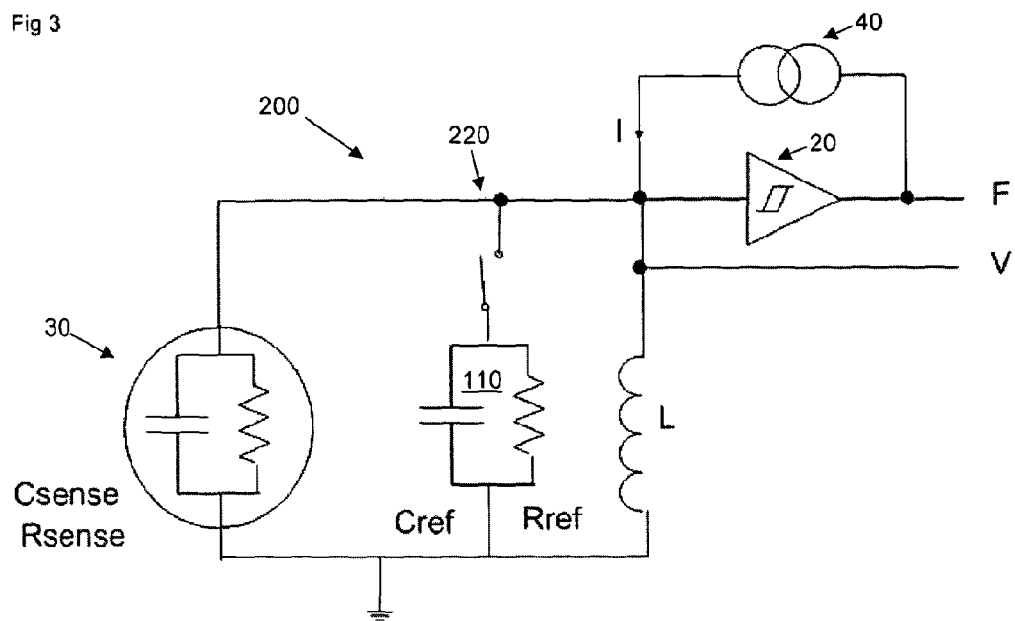
FIG. 3 shows a schematic diagram of a further circuit used to measure the real and imaginary permittivity of a sample and incorporating a reference element or circuit.

To overcome these problems, the resonant circuit, which contains the permittivity sensing element 30 may be permanently connected to the electronics and the reference circuit 110 switched in using switch 220, so that it is connected in parallel with the sensing circuit 30, as shown in FIG. 3. In this way, the main oscillation may be maintained but the oscillator frequency F and voltage V may be temporarily displaced or "nudged" by the effect of the reference circuit 110.

As with the circuit 100 described with reference to FIG. 2, the actual impedance (real and imaginary components) of the sensing circuit 30 can be expressed in terms of the reference circuit 110 impedance (real and imaginary components) independently of the electronics or other common components but the operation of the oscillator is no longer disrupted. Measurements may be obtained more quickly and reliably allowing the calculation of Csense and Rsense.

By using a reference complex impedance to temporarily displace the operating frequency F and voltage V of an oscillator it is possible to calculate more accurately the complex impedance of a sensing element 30 that is part of an oscillator system thereby reducing effects of drift and ageing. This results in improved accuracy and stability of a measuring device using such a system.

The circuit 200 described with reference to FIG. 3 may operate at radio frequencies and be a positive feedback oscillator incorporating self-calibration and wide temperature optimisation (for higher sensitivity, higher performance). This circuit 200 may be used in low-cost solutions, with low permittivity fluids, e.g. hydrocarbons and fuels.

The device solves a number of practical accuracy and performance issues that are important to achieve the level of accuracy required for certain difficult fluid sensing solutions, particularly when measuring small capacitance changes in low permittivity fluids (e.g. such as diesel quality testing and other solutions with hydrocarbons in the petrochemical industry).

In example implementations the device may be a hand-held meter or onboard a vehicle (e.g. truck, car and marine).

The device uses the principle of switching in, or "nudging" additional capacitance and/or loss to the resonant tank circuit of a marginal oscillator, as shown schematically in FIG. 3.

FIG. 3 shows a reference capacitor and resistor (Cref and Rref) forming the reference circuit 110 being added to the capacitance and inductance of the resonant tank circuit. With the value of the reference capacitor, Cref, and resistor, Rref, being known and measuring the change in frequency F and voltage V of the tank circuit (both with and without the reference components being switch in), it is possible to determine the unknown capacitance and loss of the permittivity sensing element 30 formed from Csense and Rsense.

In any practical electrical circuit, there are inherent stray capacitances and inductances and "non-ideal" performance of the components and the circuit board (PCB) tracks. Similarly, when an electrical circuit is place in an extreme or hostile environment, such as adverse changes in temperature (e.g. a 90 deg C. temperature change over the range −30 deg C. to +60 deg C.) the electrical properties or components and PCB may change. This provides further challenges for a high accuracy sensor used outside of a standard laboratory environment and typically utilised in potentially extreme and hostile environments.

Figure 4:
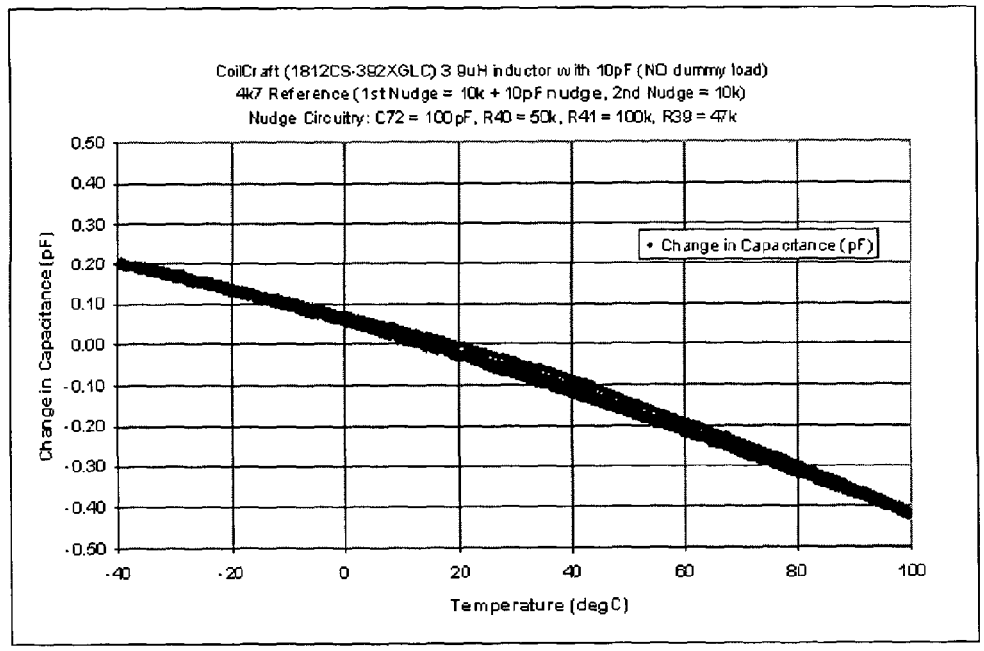
FIG. 4 shows a graphical representation of a change in capacitance with temperature of the circuit of FIG. 3.

The approach of "nudging" and switching in known reference components can improve the accuracy of sensing performance. FIG. 4 shows the improved performance achieved by utilising a small 10 pF reference capacitor (Cref) and the "nudging" approach. Sensing response over an extreme 140 degC. temperature range (−40 degC. to +100 degC.) is shown. This offers an improvement compared to a non-nudged implementation (i.e. were where inherent stability is required and reference components are not momentarily added to the tank circuit of a marginal oscillator to take differential measurements).

Using a secondary "nudging channel" it is possible to improve and optimise the sensing performance further. It is possible to improve the temperature performance of the sensing circuit by optimising the reference capacitor (Cref) value, compensating for any "non-ideal" performance of the components and circuit and provide a sensing circuit, which is inherently self-compensating to some extent.

Figure 5:
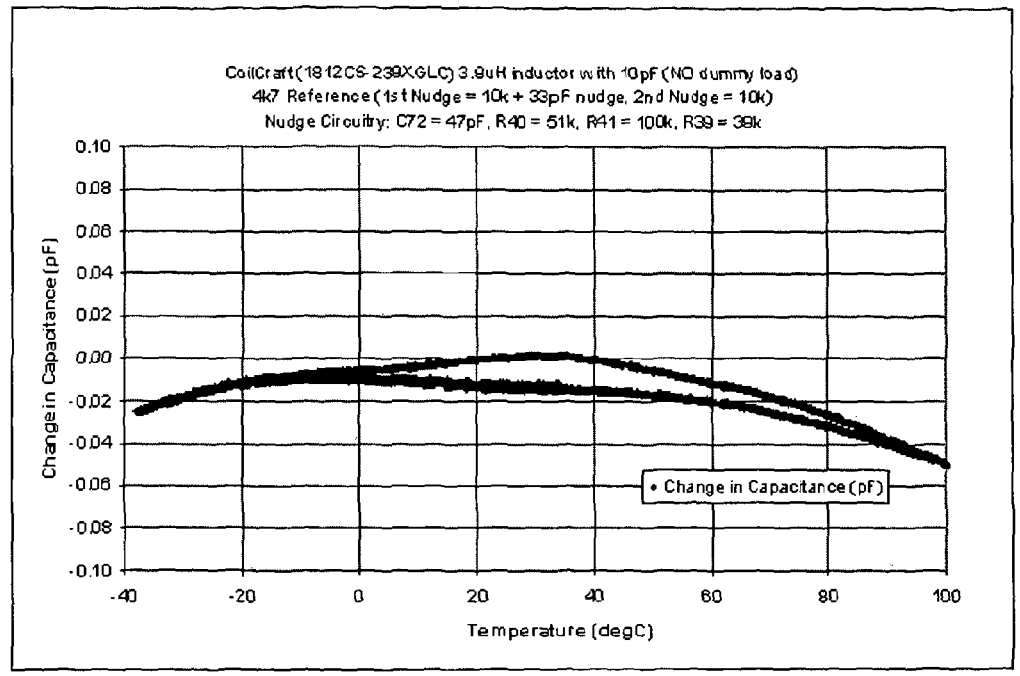
FIG. 5 shows a graphical representation of the change in capacitance with temperature of a circuit incorporating two reference elements or circuits.

FIG. 5 shows the sensed capacitance temperature response of a marginal oscillator with an optimised reference capacitor (Cref). Over a 60 deg C. range (−20 deg C. to +40 deg C.), for example, the capacitance temperature stability is within 0.01 pF, where previously (FIG. 4) the capacitance change was 0.23 pF (for the same circuit over the same temperature range), an improvement of over 20 times in this example.

Again, this improves performance and allows the measurement of smaller changes and detection of impurities in low permittivity fluids, such as diesel and biodiesel, where very small changes in permittivity and loss of the fluid are measured. Furthermore, this may be achieved in potentially harsh and extreme sensing environments (such as a low-cost hand-held field meter or onboard vehicle applications, where temperatures of −30 deg C. to +60 deg C. and beyond are readily found).

Figure 6:
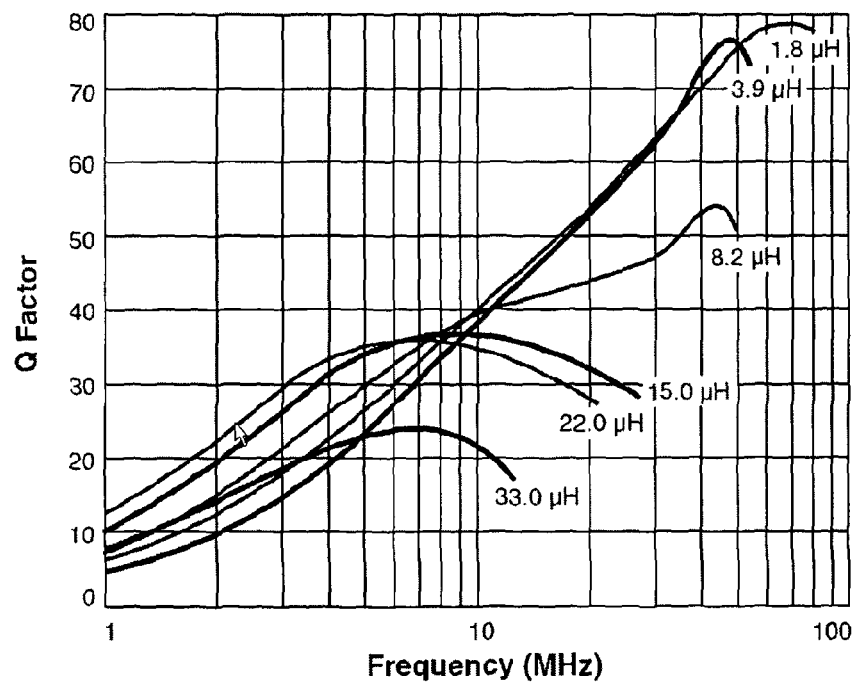
FIG. 6 shows a graphical representation of the change in quality factor with frequency of an RF inductor.

When utilising a secondary "nudging channel" it is possible to improve the performance of the sensing arrangement for both the energy stored and energy loss, reducing the need for performance trade-offs. When using just a single "nudging" channel this is not readily the case. FIG. 6 shows the response for a high performance, high Q, precision RF inductor (L). FIG. 6 shows the quality, or Q, response of the inductor, which is a measure of the inductor's quality, namely its non-ideal loss performance, with a high Q value being desirable. As seen in FIG. 6, the loss performance or Q of an inductor is not an absolute fixed value and changes with the frequency. With a sensing application where small losses, in say a fuel sample, are to be measured this is a significant consideration as changes in measured loss may be dominated by or significantly contributed to differences in the inductor's Q as a result of a change in frequency.

Figure 7:
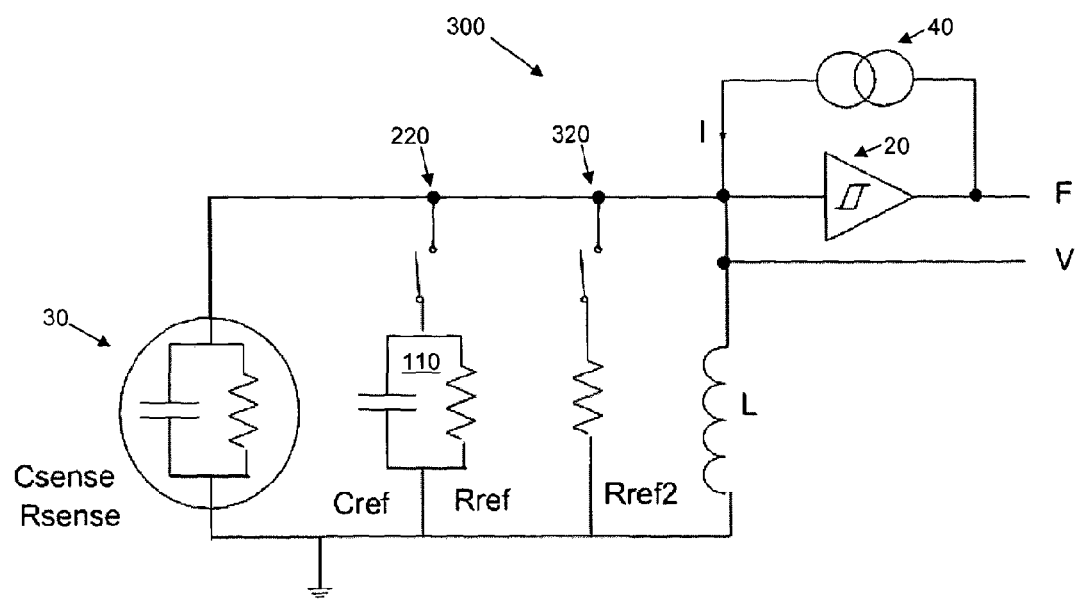
FIG. 7 shows a schematic diagram of a further circuit used to measure the real and imaginary permittivity of a sample and incorporating two reference elements or circuits.

In an example implementation of a dual "nudging channel" circuit 300 arrangement shown in FIG. 7, it is possible to "switch in" a first nudging channel with a Cref and Rref using switch 220, (whereby the reference capacitor Cref value in particular has been selected to optimise the temperature performance of the sensor's sensed capacitance), and a secondary nudging channel where a secondary reference resistor Rref2 is switched in by switch 320 in parallel to the first nudging channel or reference circuit 110. This permits very small losses of, say a fuel sample, to be readily measured (without the effect of changes of the inductor Q as a result of a significant change in frequency).

In the dual "nudging channel" circuit 300 arrangement a preferred implementation is to (1) measure the frequency and voltage of the positive feedback marginal oscillator's tank circuit, (2) switch in the first nudging channel 110 reference components (Cref and Rref) and measure the change in frequency F and voltage V, (3) switch out the first nudging channel and instead switch in the secondary nudging channel reference component(s) (Rref2) and measure the change in frequency F and voltage V. However, other schemes may be used. From the measured values, the value of the "unknown" Csense and Rsense is readily calculated. These measured values relate to energy stored and energy lost in a measured fluid sample, for example, with the geometries of a fixed sensing volume arrangement being fixed and known. Other arrangements and implementations are readily possible and can be used.

Preferably, the reference capacitor (Cref) may be an NPO temperature compensated dielectric with 1% accuracy and temperature stability of nominally 30 ppm, and similarly a reference resistor with 0.1% accuracy and 10 ppm temperature stability to enable an extremely high precision sensing solution.

This arrangement may then achieve the performance necessary for measuring small changes and impurities in low permittivity fluids, such as diesel and biodiesel and other fuels, in harsh and extreme sensing environments, such as on vehicle applications where temperatures of −30 deg C. to +60 deg C. and beyond are readily found.

As will be appreciated by the skilled person, details of the above embodiment may be varied without departing from the scope of the present invention, as defined by the appended claims.

For example, other capacitor and resistor values may be used and other samples (fluids, gases, etc) sensed.

Many combinations, modifications, or alterations to the features of the above embodiments will be readily apparent to the skilled person and are intended to form part of the invention. Any of the features described specifically relating to one embodiment or example may be used in any other embodiment by making the appropriate changes.

The invention claimed is:

1. A fluid sensor comprising:
   an oscillator having operating characteristics, wherein the frequency of the oscillator is greater than 1 MHz, the oscillator comprising driving electronics and a resonant circuit coupled to the driving electronics, the resonant circuit comprising:
   an inductor and a capacitive permittivity sensing element arranged to alter the operating characteristics of the oscillator in response to changes in permittivity presented to the permittivity sensing element;
   a first output that varies with a first operating characteristic of the oscillator as a real component of the permittivity presented to the permittivity sensing element changes;
   a second output that varies with a second operating characteristic of the oscillator as an imaginary component of the permittivity presented to the permittivity sensing element changes;
   a first reference element comprising a capacitor of known capacitance and a resistor of known resistance controllably coupled to both the inductor and the permittivity sensing element and arranged to alter the operating characteristics of the oscillator when so coupled; and
   a second reference element comprising a resistor of known resistance controllably coupled to both the inductor and the permittivity sensing element and arranged to alter the operating characteristics of the oscillator when so coupled.

2. The fluid sensor according to claim 1, wherein the oscillator is a positive feedback oscillator.

3. The fluid sensor according to claim 1, wherein the reference element is controllably coupled in parallel with the permittivity sensing element.

4. The fluid sensor according to claim 1, wherein the oscillator is arranged to drive the permittivity sensing element at a resonance frequency.

5. The fluid sensor according to claim 1 further comprising a processor arranged to compare the operating characteristics of the oscillator when the reference element is coupled to the oscillator and permittivity sensor element to the operating characteristics of the oscillator when the reference element is not coupled to the oscillator and permittivity sensor element.

6. The fluid sensor of claim 5, wherein the processor is further arranged to calibrate the permittivity sensor element based on the comparison of oscillator operating characteristics.

7. The fluid sensor according to claim 1, wherein the operating characteristics include anyone or more selected from the group consisting of frequency, amplitude, Q-factor, and phase.

8. The fluid sensor of claim 1, wherein the first operating characteristic is frequency.

9. The fluid sensor of claim 1, wherein the second operating characteristic is voltage.

10. The fluid sensor of claim 1, wherein the fluid is anyone selected from the group consisting of a gas, a liquid, a mixture of liquids, a mixture of gases, a liquid containing a solid, a gas containing a solid, a mixture of a gas or gases and a liquid or liquids, a mixture of a gas or gases and a liquid or liquids containing a solid.

11. The fluid sensor of claim 10, wherein one or more of the fluids is a fuel.

12. The fluid sensor according to claim 1, wherein the inductor and the capacitive permittivity sensing element are coupled in parallel to the driving electronics.

13. The fluid sensor according to claim 1, wherein the oscillator is a marginal oscillator.

14. The fluid sensor according to claim 1, wherein the oscillator is a Robinson marginal oscillator.

15. The fluid sensor according to claim 1, wherein the driving electronics comprises a limiting amplifier.

16. A method of measuring the permittivity of a fluid sample, the method comprising:
    driving a resonant circuit of an oscillator having driving characteristics, wherein the frequency of the oscillator is greater than 1 MHz, the resonant circuit comprising an inductor and a capacitive permittivity sensing element coupled to the inductor;
    presenting a sample to the permittivity sensing element;
    measuring a first operating characteristic of the oscillator that varies as a real component of the permittivity presented to the permittivity sensing element changes, and a second operating characteristic of the oscillator that varies as an imaginary component of the permittivity presented to the permittivity sensing element changes;
    altering the driving characteristics by controllably coupling a first reference element comprising a capacitor of known capacitance and a resistor of known resistance to both the permittivity sensing element and the inductor;
    measuring an operating characteristic when the driving characteristics are altered by the first reference element;
    altering the driving characteristics by controllably coupling a second reference element comprising a resistor of known resistance to both the permittivity sensing element and the inductor; and measuring an operating characteristic when the driving characteristics are altered by the second reference element.

17. The method of claim 16, further comprising:

decoupling the reference element from the permittivity sensing element.

* * * * *